(12) United States Patent
Lee et al.

(10) Patent No.: US 6,461,316 B1
(45) Date of Patent: Oct. 8, 2002

(54) CHAOS THERAPY METHOD AND DEVICE

(76) Inventors: Richard H. Lee, 115 N. El Camino Real, San Clemente, CA (US) 92672; Yanfang Lu, 2732 Verano Pl., Irvine, CA (US) 92612

( * ) Notice: Subject to any disclaimer, the term of this patent is extended or adjusted under 35 U.S.C. 154(b) by 0 days.

(21) Appl. No.: 09/536,623

(22) Filed: Mar. 28, 2000

Related U.S. Application Data

(63) Continuation of application No. 08/976,100, filed on Nov. 21, 1997, now abandoned.

(51) Int. Cl.[7] .................................................. A61H 23/02
(52) U.S. Cl. ........................... 601/46; 601/47; 601/48; 601/49; 601/70
(58) Field of Search .......................... 601/2, 4, 46, 47, 601/48, 49, 56, 57, 58, 59, 60, 70, 78, 79, 80, 81

(56) References Cited

U.S. PATENT DOCUMENTS

| | | | |
|---|---|---|---|
| 4,232,661 A | * | 11/1980 | Christensen ................. 601/48 |
| 4,819,616 A | | 4/1989 | Samson |
| 4,834,701 A | | 5/1989 | Masaki |
| 5,113,852 A | | 5/1992 | Murtonen |
| 5,135,468 A | | 8/1992 | Meissner |
| 5,151,080 A | | 9/1992 | Bick |
| 5,245,989 A | * | 9/1993 | Simon ........................ 601/138 |
| 5,289,438 A | | 2/1994 | Gall |
| 5,506,795 A | | 4/1996 | Yamakawa |
| 5,611,771 A | * | 3/1997 | Taylor ......................... 601/70 |

FOREIGN PATENT DOCUMENTS

LU    85 1 00622    7/1986

OTHER PUBLICATIONS

Measurement and analysis of Infrasonic Waves from the Emitted Qi, 1988 Niu Xin, et al.

* cited by examiner

Primary Examiner—Danton D. DeMille

(57) ABSTRACT

A therapy device, in its preferred embodiment, incorporates a chaos signal generator into a therapeutic massager for the purpose of increased therapeutic effectiveness in such areas as pain management, inducing calm, increasing mental clarity, interrupting repeating thoughts and emotions, and enhancing states of human awareness, such as mental analysis and intuitive functioning, by applying specific frequency bands of a highly unpredictable chaotic signal.

9 Claims, 3 Drawing Sheets

Treatment Frequency Bands included
in the preferred embodiment (Hz)

CHAOS THERAPY METHOD AND DEVICE

CROSS REFERENCE TO RELATED APPLICATION

This is a continuation of U.S. application Ser. No. 08/976,100, filed on Nov. 21, 1997 now abandoned. The priority of this prior application is expressly claimed and its disclosure is hereby incorporated by reference in its entirety.

FIELD OF INVENTION

This invention relates to therapeutic devices, specifically to a therapeutic massager and a signal generator for such massager.

BACKGROUND OF THE INVENTION

Electric and electromechanical therapy devices are intended to improve patient or user well-being, including relieving pain, promoting relaxation; accelerating recovery, and inducing desired states of consciousness.

Such therapy devices can be classified in three areas:

In the first area the devices deliver therapeutic signals which are modified or combined to increase therapeutic effectiveness. Exemplary devices are the following:
- U.S. Pat. No. 4,834,701 to Masaki (1989) shows a device which generates a varying therapeutic signal by combining two acoustical signals to produce a low frequency "beat frequency" signal which is applied acoustically to a patient to alter the frequency of the brain's electrical signals. These changes reduce beta rhythm (14 to 20 Hz activity) to alpha rhythm (8 to 14 Hz), as measured by an electroencephalograph (EEG).
- U.S. Pat. No. 5,113,852 to Murtonen (1992) shows a device which generates a varying therapeutic signal and applies it to a human body through several speakers mounted in a chair. The applied audio energy provides phase angle variations throughout the body.
- U.S. Pat. No. 5,289,438 to Gall (1994) shows a device which combines several recorded brain wave signals and delivers them to the subject through headphones. This sound is used to induce altered brainwave rhythms.
- U.S. Pat. No. 5,151,080 to Bick (1992) shows a device which adds distortion to an audio signal through an electronic "robot voice" type synthesizer. This sound is used to increase the effectiveness of hypnotic suggestion.

The first area also includes subliminal message systems such as audio music and sound systems, flickering light systems, and electrodermal systems which deliver complex signals to the body. While these therapy devices do provide a broader and more varying spectral distribution of signal frequencies, the resulting signals become familiar, and hence, predictable. Thus the body can anticipate them and filter them out. This predictability limits their effectiveness.

In the second area therapy devices use random noise for simulating signals observed in nature. Such devices are shown in the following: U.S. Pat. No. 4,819,616 to Samson (1989) shows a device which uses a white noise generator to simulate the sound of a mother going "sshhhhh" to calm a baby. Another product which uses random noise lulls people to sleep with the sound of ocean waves or waterfalls created by white noise. Yet another product is a white noise generator for offices which increases background noise to make distracting noises less audible. Because the white noise is not made different from background noise, it simply adds to the ambient white noise which is produced from background sources such as fans in electronic equipment, air vents, running water, wind, and the blending of outdoor sounds. Thus, there is little therapeutic value to unshaped white noise beyond raising the ambient noise to decrease our auditory threshold to distracting noises.

In the third area, devices use an electronic feedback loop to simulate a signal in nature. An FDA-listed therapeutic massager, manufactured by China Healthways Institute of San Clemente, Calif., has been sold under the trademark INFRATONIC QGM for eight years and simulates the subsonic sound output from the hands of energy healers. This device, based on Chinese research, incorporates a small degree of noise in a resonating circuit in order to simulate a signal emitted from the hands of energy healers. A summary of this research was presented at the First World Conference for Academic Exchange of Medical Qigong. This summary is entitled "Measurement and Analysis of the Infrasonic Waves from the Emitted Qi", Niu Xin, et al., Beijing College of Traditional Chinese Medicine, 1988.

This device incorporates a feedback loop including a noise generator and a high-pass/low-pass filter which approximates the shape and frequency band of the irregular waveform of the healers' signal. A noise generator excites the non-linear filter feedback loop. This excitation prevents the signal from decaying or falling into obviously sinusoidal or otherwise repeating patterns. While this feedback loop does produce some randomness, the produced signal is dominated by the high-pass/low-pass filter system, and is thus dominated by the repeating modes of resonance which the filter supports. Much like a car with a fouled spark plug or a railroad train traveling over varying segments of track, the signal is highly repeatable with a small random component. While effective, the Infratonic QGM has considerable room for improvement because:

1) The circuit is dominated by the filter/feedback loop. Here, small variances in capacitors and other circuit parameters alter the modes of resonance from unit to unit. Thus, small variations in component value and function have strong influence on the output waveform. Thus output waveform varies considerably from unit to unit.
2) Attenuation of bandwidth is gradual. This circuit was designed to produce a signal between 4 and 16 Hz, peaking at around 10 Hz, and produces significant output outside of the range of Alpha, which is 8 to 13 Hz. This lack of precision in producing the desired frequency band limits effectiveness.
3) Amplitude is not controlled. High spikes of random noise occasionally overload the high-pass/low-pass filter and create transient spikes which result in current surges and cause the speaker to "bottom out", creating unpleasant noises and undue wear on the equipment.
4) The circuit is dominated by the band-pass filter which favors repeating patterns in the output signal. If noise input is too low, or band-pass filter is too dominant, this signal slips into recognizably repeating patterns, and discrete frequencies dominate. Thus, broad spectrum frequency output is difficult to maintain.
5) While the signal produced by this device does contain some random noise, as do the therapeutic signals produced by many of the devices described above, a recognizable and therefore predictable pattern dominates. This predictable pattern limits the effectiveness of this device.

As reflected in the above prior art, although complexity, distortion, and randomness have been added to therapy devices, because of the predominantly predictable nature of these signals, the human body can anticipate them and filter them out, and thus they are considerably less than optimally effective.

Specific methods for producing a highly unpredictable signal not associated with therapeutic application are known, e.g., U.S. Pat. No. 5,506,795 to Yamakawa (1996) shows a means of producing a randomly behaving signal.

SUMMARY OF THE INVENTION WITH OBJECTS

In accordance with the present invention, a therapy device, in its preferred embodiment, incorporates a chaos signal generator into a therapeutic massager for the purpose of increased therapeutic effectiveness in such areas as pain management, inducing calm mental clarity, interrupting repeating thoughts and emotions, and enhancing states of human awareness, such as mental analysis and intuitive functioning, by applying specific frequency bands of a highly unpredictable chaotic signal.

Objects and advantages of the present invention are:

(a) to provide an improved therapeutic stimulating device, (b) to provide a therapeutic massager with an improved circuit which is capable of delivering a signal with a high degree of randomness without problems of circuit instability, (c) to provide an improved therapeutic massager which provides higher effectiveness by delivering a more unpredictable signal which can not be anticipated by the human body and thus penetrates past the body's defenses for deeper and more penetrating therapy (as defined below), and (d) to provide a therapy device which can precisely produce a chaotic signal of virtually any desired frequency band, and produces minimal power outside that frequency band, allowing the application of specific frequency bands for different conditions.

Further objects and advantages will become apparent from a consideration of the ensuing description and drawings.

DETAILED DESCRIPTION OF A PREFERRED EMBODIMENT

Figure 1A:
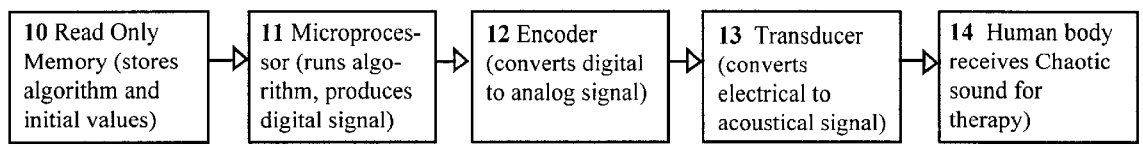
FIG. 1A shows a block diagram of a chaos therapy device in accordance with my invention.

FIG. 1 shows a block diagram of a therapy device in accordance with the invention. A read-only memory chip 10 (EPROM 27C64 or 27C512) stores algorithm and initialization data and feeds it to a microprocessor 11 (Intel 80C31), which runs the algorithm, producing a digital chaotic signal.

Because the unpredictable nature of a therapeutic signal is central to this device, I have used the term "chaos" to describe a signal whose pattern is so unpredictable that it has increased effectiveness as a therapeutic signal. Thus a "highly chaotic signal" is one which changes so randomly that the human body can anticipate very little of it, and therefore is incapable of selectively ignoring it or actively canceling it out. This is what allows such a signal to penetrate past the body's defenses. A slightly chaotic signal may appear random because specific patterns do not repeat, but can contain a strong basic rhythm which becomes familiar and can be filtered out. As an example, the rhythm produced by a train as it passes over the track from rail to rail is a constantly varying signal because rails vary in length, cross ties vary in height and firmness of foundation, and the train varies in speed. Yet the pattern soon becomes very familiar, and thus becomes highly predictable and can be filtered out. This signal, and the signal produced by the Infratonic QGM above, while non-repeating, are not "highly chaotic" as the term is used in this specification because they are, for the most part, predictable by the body.

An encoder 12 (DAC0832) converts the digital chaotic signal into an analog voltage. A transducer 13, a loudspeaker with a weighted cone to lower frequency response so as to be able to deliver infrasonic sound, converts this analog voltage into an acoustical signal which is delivered to a human body 14. This loudspeaker is similar to a standard three-inch diameter speaker except that the cone consists of a brass core suspended with a rubber diaphragm. The power level delivered to this speaker is selectable at the panel at levels of approximately 1, 2, and 4 watts.

Figure 1B:
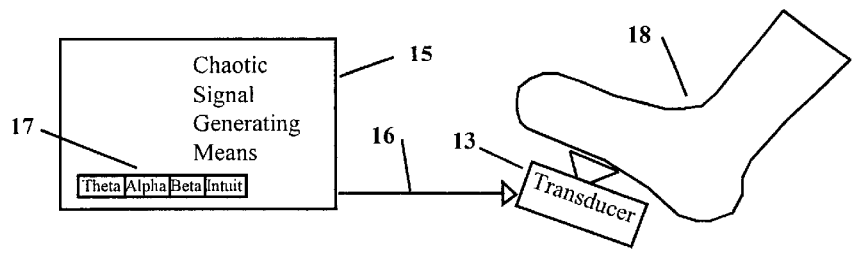
FIG. 1B shows a typical application of the chaos therapy device.

FIG. 1B shows the chaos therapy device applied to the plantar surface of a patient's foot 18. Chaotic signal generator 15, which is made up of read-only memory 10; microprocessor 11, and encoder 12, has four buttons 17 on its front panel which are depressed to select a specific algorithm for the desired frequency band. Cable 16 delivers the selected signal to transducer 13, which, in this drawing, is applied to foot 18.

Figure 2A:
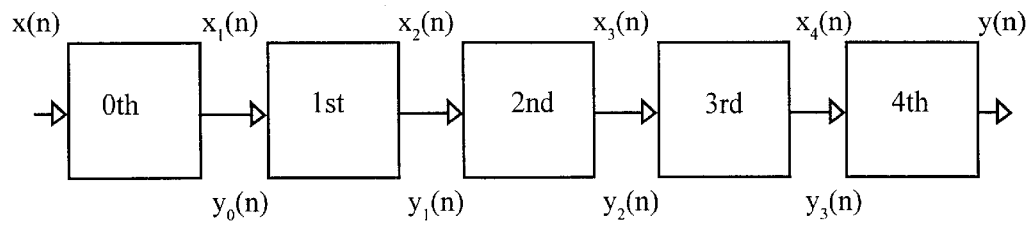
FIG. 2A shows a block diagram of the five stage digital filter of the chaos therapy device.
Figure 2B:
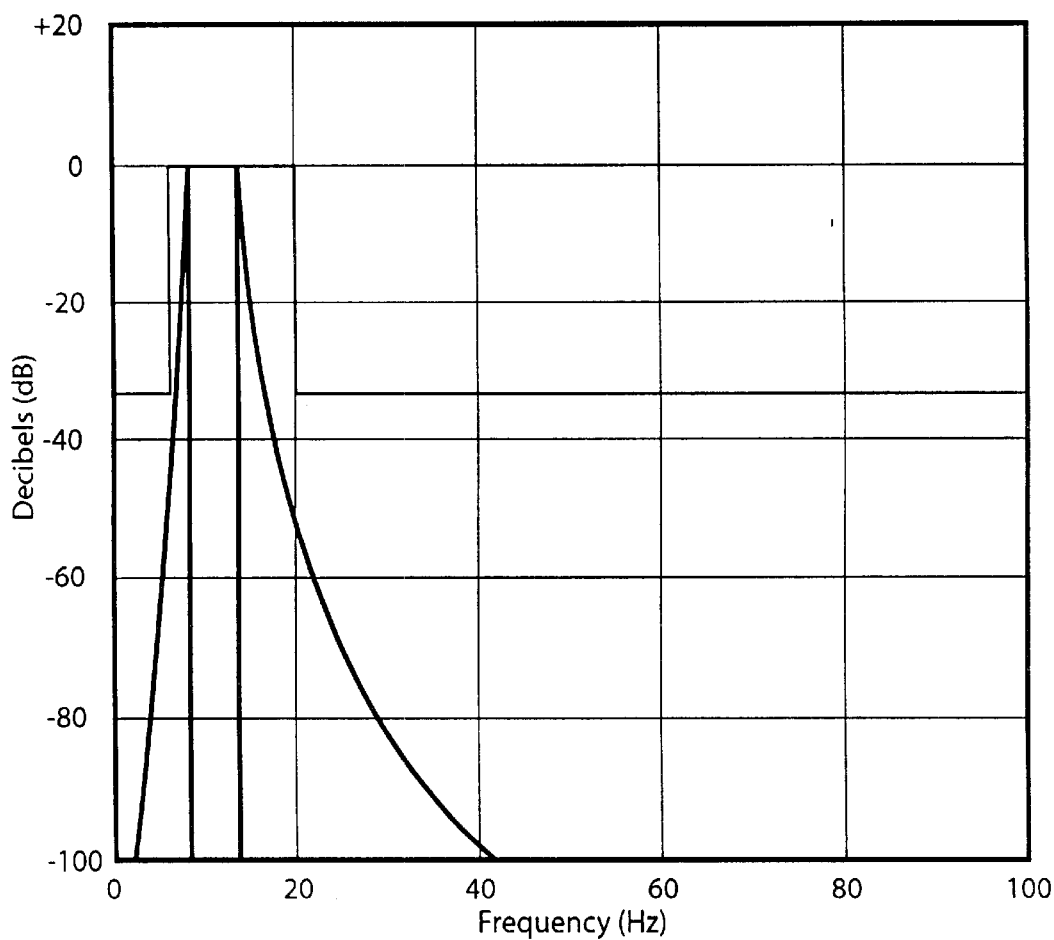
FIG. 2B shows a plot of the response, y(n) of the digital filter of the chaos therapy device.
Figure 2C:
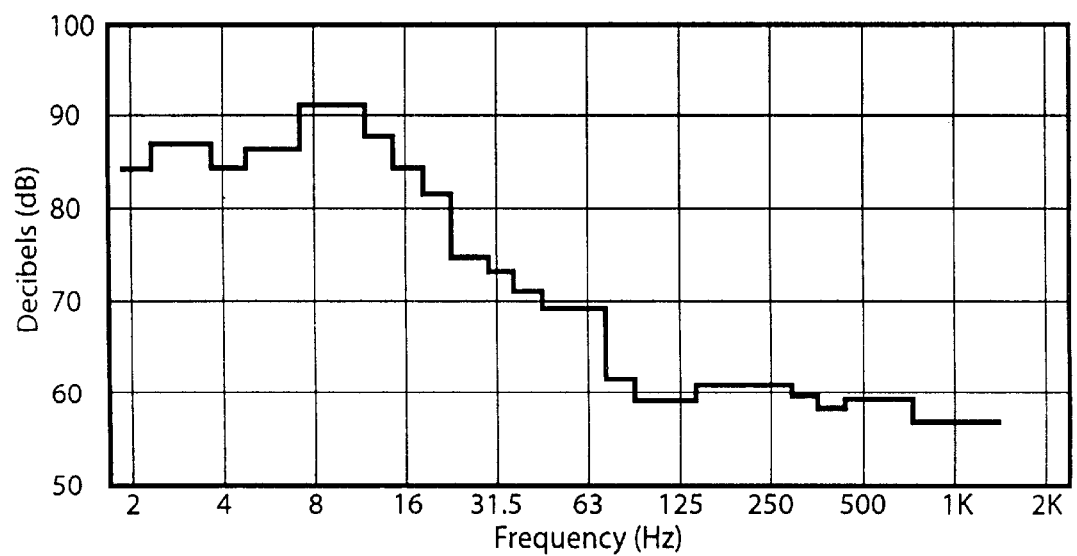
FIG. 2C shows a plot comparable to FIG. 2B, except that it shows the output from the Infratonic QGM.

Description—FIGS. 2A–2C—Generation of Chaotic Signal

The algorithm producing the signal is as follows. First, a random data stream is produced by means of the algorithm of congruence, a prior-art algorithm for producing random numbers as described in the book, Digital Signal Processing by Alan V. Oppenheim and Ronald W. Schafter, Prentice-Hall, Englewood Cliffs (Chapter 5, P 195–283)

The generated random data sequence is then passed through a Chebyshev type I IIR five-stage digital filter, as defined on page 6.1–2 of the book, Programs for Digital Signal Processing, Digital Signal Processing Committee, IEEE Acoustics, Speech and Signal Processing Society, Chapter 6, 1979.

Designing a random number generator and a digital filter to convert the random data sequence into a chaotic signal with the desired bandwidth characteristics is straightforward circuit design exercise for those knowledgeable in the design and programming of digital signal processing equipment. Specifics of this design are as follows:

a) To generate the noise signal, random noise is generated according to the algorithm of congruence as in the following program segments of C language. First the variable rn is initialized as:

$rn=2*(int)pow(2,14)-2)+1$

Next, random noise is generated through this circulation:

rn=(float)*259;

rn=rn−(int)(rn/32768)* 32768;

rstn=rn rstn=rstn/32768 sn [i]=(b−a)*rstn+a (a is the lower limit 0 and b is the upper limit 32768)

rn=sn[i] (sn[i] is the resultant random number sequence)

A series of five digital filters is used as shown in FIG. 2A, where x(n) is the random noise s(n) generated above and y(n) is the resultant chaotic signal. The input of the ith filter at the moment n is $x_i(n)$ and its output is $y_i(n)$. The relation between input and output for every filter is below:

$$y_i(n) = \sum_{k=0}^{2} B(I,k) * x_i(n-k) - \sum_{k=0}^{2} A(I,k) * y_i(n-k).$$

The variables B(I,k) (k=0,1,2) and A(I,k) (k=1,2) are the kth order coefficients of the ith filter. Accordingly the design calculations are shown below:

Infinite Impulse Response (IIR) Chebyshev I Bandpass Filter Unquantized Coefficients:

Filter order=10

Sampling frequency=1 kHz

| I | A(I,1) | A(I,2) | B(I,0) | B(I,1) | B(I,2) |
|---|---|---|---|---|---|
| 1 | 1.981052 | .985126 | .007462 | .000000 | −.007462 |
| 2 | −1.980481 | .986138 | .014799 | .000000 | −.014799 |
| 3 | −1.986848 | .989767 | .009985 | .000000 | −.009985 |
| 4 | −1.987443 | .994228 | .022028 | .000000 | −.022028 |
| 5 | 1.004040 | .996535 | .012008 | .000000 | −.012008 |

Characteristics of designed filter:

|  | Band 1 | Band 2 | Band 3 |
|---|---|---|---|
| Lower band edge | .00000 | .00800 | .02000 |
| Upper band edge | .00600 | .01300 | .50000 |
| Nominal gain | .00000 | 1.00000 | .00000 |
| Nominal ripple | .02000 | .02000 | .02000 |
| Maximum ripple | .00674 | .08273 | .00159 |
| Ripple in dB | −43.42926 | .69037 | 55.98095 |

The coefficient A(I,k) and the response are plotted in FIG. 2B. This the design of the signal generator is a common digital circuit design which follows from the above cited references.

FIG. 2C shows the output of the Infratonic QGM device, which shows a fundamental difference from the output of the chaos therapy device. Note that the attenuation of this signal is gradual, with frequency of signal output at 10 dB below the desired band ranging between 0 and 24 Hz. FIG. 2B shows that the frequency range of the chaos therapy device attenuates much more quickly, with the range at 10 dB below the desired band staying between about 7 and 15 Hz. The clearly defined band width of the chaos therapy device (FIG. 2B) is a key aspect of its improved effectiveness. Reports from doctors who have used both the chaos therapy device and the Infratonic QGM in their practice emphasize that the chaos therapy device, while similar in application to the Infratonic QGM, is many times as effective.

Figure 3:
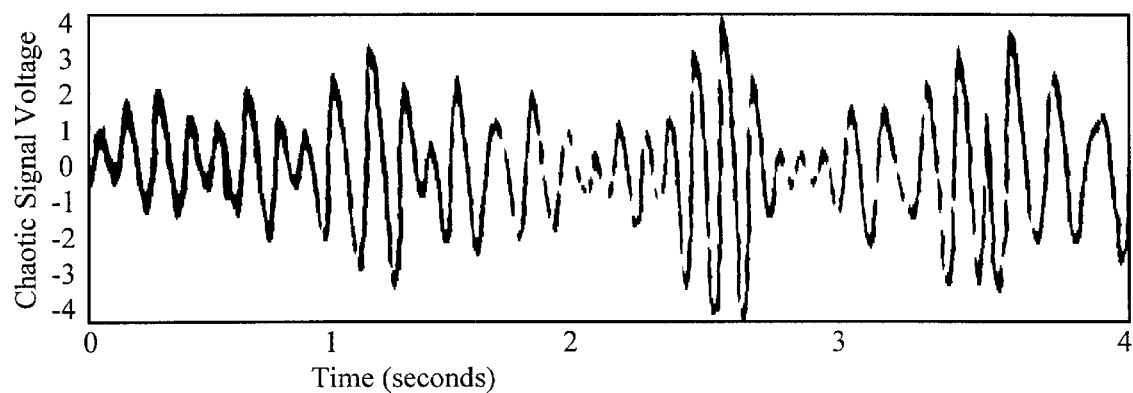
FIGS. 3 and 4 show a typical chaotic signal and power spectrum of that signal during application of the chaos therapy device.
Figure 4:
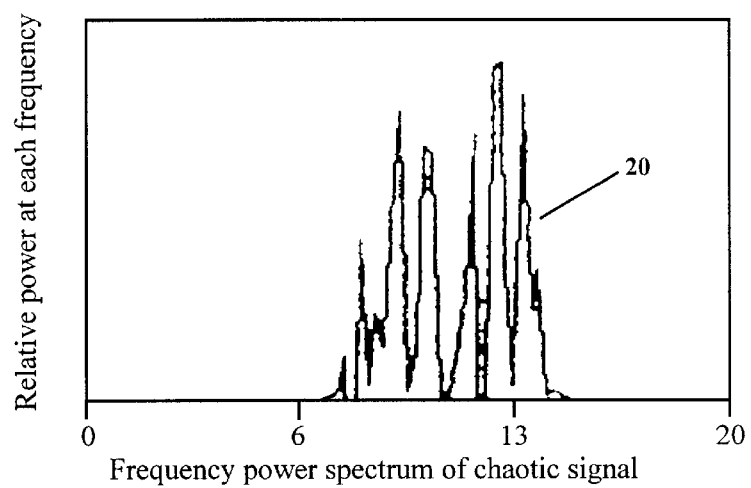
Figure 5:
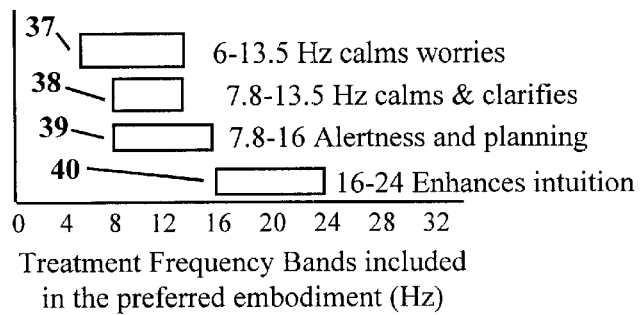
FIG. 5 shows different frequency ranges of trembling vibration, and frequency ranges of treatment in the preferred embodiment of my chaos therapy device.

Operation—FIGS. 3 to 5

FIG. 3 shows a four-second sample of a signal from chaotic signal generator 15 while producing band 38 as shown in FIG. 5. Note that this signal has unpredictable variations in both frequency and amplitude.

FIG. 4 shows a frequency power spectrum of the voltage output. Note that the frequency spectrum produced lies in the desired range of 7.8 to 13.5 Hz, and that power at frequencies outside this range is minimal. The variation in power density within this range is due to the chaotic nature in a four-second signal.

FIG. 5 shows the four selectable frequency bands of chaotic sound included in the preferred Xf embodiment. The first band 37, 6–13.5 Hz, induces deep relaxation, decreases the worry and stress of excess Beta activity, provides sedative-like pain relief, and induces pre-surgical anesthesia. The second band 38, 7.8 to 13.5 Hz, induces calm clarity, provides pain relief and accelerated healing, and decreases both the desires of Theta and the worries of Beta. The third band 39, 7.8 to 16 Hz, enhances analytical functioning, accelerates post surgical recovery, and acts somewhat like a stimulant such as coffee to increase alertness. The fourth band 40, 16 to 24 Hz, includes both high analytical frequencies (16 to 20 Hz) and the intuitive band (20 to 24 Hz). It improves problem-solving ability and increases intuitive functioning. The ability to deliver a chaotic signal within a specific frequency range without delivering significant signal energy in adjacent ranges is one of the principal ways that the chaos therapy device provides improved performance over prior-art devices. This is accomplished with the five-stage digital filter shown in FIG. 2A.

The device is generally applied to the area of pain, injury or illness. It can also be applied to energy centers, such as the center of the chest for enhanced immune response or lung activity, to the solar plexus for digestive weakness, or to the navel for increased energy. The signal most commonly selected is signal 38 as shown in FIG. 5 because signals in this range bring the patient into a state focusing on the physical body and away from thoughts and emotions. Signals in band 37 are selected where excess Beta activity (thoughts) is responsible for more acute pain or excess worry and stress. Signals in band 39 are selected where the patient appears slow and mentally dull, and thus is in the semi-unconscious emotional state of Theta. This improves mental functioning. Signals in band 40 are applied where people are seeking enhanced intuitive functioning, and thus band 40 is used principally for accelerating development of higher consciousness.

Safety and Efficacy

The Infratonic QGM device has been listed by the FDA as a 510k therapeutic massager since 1992. When applied to the point of pain, it infuses the body with full spectrum sound in the general range of the Alpha rhythm and induces pain relief, relaxation, and mental clarity. It can be applied to any part of the body and is typically applied to the chest, abdomen or plantar surface of foot for relaxation and mental clarity. About 1% of all doctors in the United States now use this device in their practice and have reported no problems with safety. The present chaos therapy device also produces a sound signal, but with a precisely defined frequency bandwidth and a high degree of chaos. No adverse effects have been identified in product testing, nor are they anticipated.

Conclusions, Ramifications, and Scope

The chaos therapy device provides several advantages. In addition to providing a highly chaotic signal which penetrates more deeply than predictable signals, the chaos therapy device also provides a precisely defined frequency band which increases effectiveness where induction of specific brain rhythms is therapeutically effective. While in the preferred embodiment these principles have been applied to a therapeutic massager, they can be applied broadly to therapy devices and process equipment of many kinds.

A principal advantage over therapy devices using common therapeutic signals like sine waves, square waves, and impulse functions, using complex or combined waveforms, and using noise generators to excite resonating filters, is that the computerized algorithm of this chaos therapy device produces a highly chaotic, unpredictable signal. While these other signals all contain some degree of noise, none contain sufficient unpredictable noise to sufficiently enhance therapeutic effectiveness to have this important factor recognized. The reason that this increased chaos enhances effectiveness is that a signal, which is unpredictable, cannot be filtered out by the human body. Thus the chaotic signal penetrates deeply through the defenses of the body, reaching deeper to relieve pain and helping people let go of mental and emotional patterns that are often a source of illness, discomfort, and slow recovery.

Another important benefit of the chaos therapy device is that it can produce precisely defined frequency bands of chaotic sound, producing physiological effects such as enhancing the Alpha rhythm while decreasing the Theta rhythm. A device that delivers the desired band, but also delivers some power in adjacent bands will be less effective at achieving this result. In addition, a device which delivers a predictable signal will be less effective. Thus these two effects, high chaos and precise frequency bands, work synergistically for enhanced effectiveness.

Although the description above contains many details, these should not be construed as limiting the scope of the invention, but merely as providing illustrations of some of the presently preferred embodiments. Other embodiments are possible, such as the following:

1) Shaping the Chaotic Signal

Limiting a chaotic signal to specific frequency bands is just one way of shaping it. Here are examples of others: a) The notes of a chord can be fluctuated chaotically. b) A single note can be varied in frequency or intensity according to a chaotic signal. c) The same note can be played at different octaves each modulated chaotically. d) A chaotic frequency band can be generated which excludes a specific frequency or small frequency band. e) Chaotic color therapy might have three colored lights vary in intensity to provide a modulating color delivering specific frequency bands. f) A chaotic signal can be combined with a highly shaped signal. g) Impulses delivered by a transcutaneous electrical stimulation device can be randomly timed and have randomly varying amplitude. h) The delivered frequency band can be varied chaotically in frequency and the amplitude of a signal can be varied chaotically.

2) Additional Therapeutic Applications:

Therapeutic massagers are not the only devices to benefit from this chaos therapy method. Transcutaneous Electrical Nerve Stimulation (TENS), diathermy, magnetic resonance, and therapeutic ultrasound are examples of products which will show enhanced effectiveness when chaos is added to the delivered signal. Also, brain/mind machine applications are possible, such as audio tapes, flashing lights, or any product which can deliver a chaotic signal.

Shaping chaotic signals to other frequency bands will produce therapeutic effectiveness. Examples are the range of 20 to 40 Hz, the physical sound produced by the heart, and the range of 800–1400 Hz associated in psychic research with the "astral body" when it is white in color. Chaotic frequency bands can be used in ranges from the deep infrasound to ultrasound, mega, and gigahertz ranges.

3) Processes That Can Be Improved Through Application of Chaotic Signals

Vehicles: Chaotic signals can be used to enhance alertness and mental clarity for drivers of cars and airplanes and for operating dangerous equipment. Cars can be fitted with devices which generate chaotic noise in the Alpha range to make the ride seem smoother and more pleasant. The airflow in the passenger cabin of jets can be modulated chaotically to include infrasonic pressure waves to reduce the side effects of a monotonous hiss and to help relax the passengers.

Environmental conditioning: Air conditioning fans in large buildings can be modulated through inlet vanes or pressure dampers to induce infrasonic pressure waves throughout the building to relax employees, provide increased clarity of thinking, reduce focus on emotional concerns, improve health, and reduce absenteeism. Air ionizers (negative ion generators) can be modulated to apply chaotic waves of varying electric potential for room occupants.

Task oriented applications: Computer screens can introduce a chaotic signal to users by chaotically varying the background color or other attributes to reduce stress and increase mental clarity (7.8–13.5 Hz.), to increase analytical focus (7.8–16 Hz.), or to enhance creativity (16–24 Hz.). In stores, chaotic signals can increase customer comfort and influence mood. In schools chaotic signals can bring students to states of mental clarity or analytical preparedness. And in factories, chaotic signals can help maintain mental clarity for reduced occupational injuries.

Heavy impact equipment: By chaotically varying the impact of jackhammers, pile drivers, and earth compacting equipment, the ground will be more yielding because variation helps more than repetition to penetrate resistant areas.

Entertainment: Chaotic signals can intensify the emotional highs and lows and feelings of inspiration induced by movies and high-end amusement park rides. In addition, chaotic frequency bands or chaotic variations can be used in audio equipment to provide a new dimension in audio entertainment. Chaotic sounds can also be applied to subliminal TV and radio advertising techniques to enhance desire and decrease analytical functioning.

Pollution control: Frequency bands of chaotic sound can be used to alter the nature of the particulates which form in exhaust stacks after combustion or other processes.

Sedation devices: Chaos-based devices to help people sleep and to calm animals, such as a "Chaos Collar" to calm an overactive dogs, will prove highly effective.

Bioactivity. Chaotic sound generating systems will strengthen agricultural crops, provide pest control, and improve yield in biochemical processes. A simple example is in raising bread with yeast. Chaotic sounds can also be applied to improve the flavor of food through such means as consumer cooking equipment. Another example is ultrasonic rodent and bug repellants that work better or provide the same effect on insects and rodents without annoying people and dogs so much.

Balancing or calming the earth itself: The earth's magnetic field has strong magnetic micropulsations in the range of 0 to 30 Hertz, roughly the same as the range of human brain waves as measured by EEG. And the resonant frequency of the earth's surface to radio waves 7.8 Hz, is, the same frequency as the boundary between the Theta and Alpha rhythms of the EEG. This is the boundary between subconscious emotions and calm mental clarity. Thus large-scale production of chaotic Alpha activity will calm emotional turbulence (Theta) in the earth. And by introducing this signal in areas of the world overwhelmed by human conflict, peace between warring nations can be more easily achieved.

Also, chaotic signals can be applied to computer systems to increase creativity of artificial intelligence, in fluid dynamics to induce turbulence to reduce drag, in chemical processes to drive reactions toward otherwise improbable chemical compounds, or to raise bond energies above threshold levels without destructive heat. Chaotic signals can be applied to the breaking up of separative attitudes among metastasized cancer cells, bringing the body into harmony and aiding in the recovery from cancer.

Thus, the scope of the invention should be determined by the appended claims and their legal equivalents, rather than by the examples given.

What is claimed is:

1. A therapy device comprising:
   a signal generator for generating a chaotic signal having a time varying frequency, a time varying amplitude, and a frequency power spectrum associated therewith, said chaotic signal being generated over a predetermined frequency band wherein minimal power from said frequency power spectrum falls outside said predetermined frequency band; and
   signal induction means for receiving said chaotic signal and for applying said chaotic signal to a living body.

2. The therapy device of claim 1 wherein said predetermined frequency band is selected from the group consisting of the approximate frequency ranges of 6 to 13.5 Hz, 8 to 13.5 Hz, 8 to 16 Hz, and 16 to 24 Hz.

3. The therapy device of claim 1 wherein said predetermined frequency band has a bandwidth of less than one octave.

4. The therapy device of claim 1 wherein said predetermined frequency band is user selectable.

5. The therapy device of claim 1 wherein said signal induction means comprises a sonic transducer.

6. A therapy device comprising:
   a signal generator for generating a chaotic signal having a time varying frequency, a time varying amplitude, and a frequency power spectrum associated therewith, said chaotic signal being generated over a predetermined frequency band of less than one octave, and wherein minimal power from said frequency power spectrum falls outside said predetermined frequency band of less than one octave; and
   signal induction means for receiving said chaotic signal and for applying said chaotic signal to a living body.

7. The therapy device of claim 6 wherein said predetermined frequency band is selected from the group consisting of the approximate frequency ranges of 6 to 13.5 Hz, 8 to 13.5 Hz, 8 to 16, Hz, and 16 to 24 Hz.

8. The therapy device of claim 6 wherein said predetermined frequency band is user selectable.

9. The therapy device of claim 6 wherein said signal induction means comprises a sonic transducer.

* * * * *